United States Patent [19]  
Krevald

[11] Patent Number: 4,732,754  
[45] Date of Patent: Mar. 22, 1988

[54] METHOD FOR THE PREPARATION OF ANTIPERSPIRANT COMPOSITIONS HAVING ENHANCED EFFICACY

[75] Inventor: Helga Krevald, Tarrytown, N.Y.

[73] Assignee: American Cyanamid Company, Stamford, Conn.

[21] Appl. No.: 818,383

[22] Filed: Jan. 10, 1986

Related U.S. Application Data

[63] Continuation of Ser. No. 591,888, Mar. 21, 1984, abandoned, and a continuation of Ser. No. 353,730, Mar. 1, 1982, abandoned.

[51] Int. Cl.$^4$ .......................... A61K 7/34; A61K 7/38  
[52] U.S. Cl. ................. 424/66; 424/DIG. 5; 424/68  
[58] Field of Search ................ 424/68, 66, DIG. 5

[56] References Cited

U.S. PATENT DOCUMENTS

| | | | |
|---|---|---|---|
| 3,472,940 | 10/1969 | Osipow et al. | 424/73 X |
| 3,541,205 | 11/1970 | Hardigan et al. | 424/184 |
| 4,229,432 | 10/1980 | Geria | 424/DIG. 5 |
| 4,264,586 | 4/1981 | Callingham et al. | 424/68 |
| 4,268,499 | 5/1981 | Keil | 424/68 |
| 4,280,994 | 7/1981 | Turney | 424/DIG. 5 |
| 4,350,605 | 9/1982 | Hughett | 424/68 |

FOREIGN PATENT DOCUMENTS 2013085 8/1979 United Kingdom ................. 424/68

Primary Examiner—Dale R. Ore  
Attorney, Agent, or Firm—C. J. Fickey

[57] ABSTRACT

Improved antiperspirant compositions having an astringent material suspended in a hydrophobic medium, and emulsions of aqueous solutions of astringent materials in a hydrophobic medium, said compositions having added thereto from 1 to 5% by weight of a $C_3$ to $C_8$ alkanediol compound.

10 Claims, No Drawings

METHOD FOR THE PREPARATION OF ANTIPERSPIRANT COMPOSITIONS HAVING ENHANCED EFFICACY

This application is a continuation of application Ser. No. 591,888, filed Mar. 21, 1984, and a continuation of Ser. No. 353,730, filed Mar. 1, 1982, now both abandoned.

The present invention relates to a method for improving the efficacy of antiperspirant compositions containing an antiperspirant astringent compound. More particularly, it relates to improvements in the antiperspirant efficacy of suspensions and emulsions of an astringent compound in a hydrophobic medium.

Antiperspirants are well-known both in the prior art and in the marketplace. Historically, they have been of two principal types—the solution type and the alcohol-in-water type, both of which have disadvantages. The former, which have long been known to be more efficacious than dry powders or alcohol solutions, are tacky and greasy on drying; the latter have been perceived to be cold on application and cause a stinging sensation due to the alcohol.

Antiperspirant sticks, wherein the antiperspirant astringent compound is suspended or dispersed in a low melting, water-insoluble waxy material, and mixtures of waxy materials with both water-soluble and water-insoluble emollients, are known; see, for example, U.S. Pat. No. 4,049,792. More recently, antiperspirants of the "dry feeling" type have been offered. These usually comprise a suspension of the astringent compound in a hydrophobic vehicle, such as a volatile silicone, or an emulsion of an aqueous solution of an astringent in a similar vehicle as the continuous phase.

Davy et al, U.S. Pat. No. 4,126,679, and Geary et al, U.S. Pat. No. 4,151,272, describe antiperspirant stick compositions comprising a suspension of an astringent in a waxy matrix containing a waxy material and volatile silicone. In an attempt to improve the efficacy of suspension type antiperspirant sticks, Geary, in a commonly assigned, copending application, Ser. No. 195,563, filed Oct. 9, 1980, now abandoned, found that the addition thereto of relatively high concentrations of certain esters of alkanediols, for example, 1,3-butanediol lactate, enhanced the efficacy.

Gee et al, U.S. Pat. No. 4,122,029, and Keil, U.S. Pat. No. 4,265,878, describe water-in-oil emulsions of an aqueous solution of an astringent in a non-polar continuous phase, for example, a volatile silicone. These compositions are reported to exhibit the desired "dry feel" and to have improved efficacy.

The trend in antiperspirant development has been to obtain compositions which exhibit the efficacy of aqueous solutions of astringent, such as aluminum chlorohydrate, but which avoid the unpleasantness associated with their use. Suspensions of astringent in a hydrophobic medium, exemplified by a volatile silicone, and water-in-oil emulsions of aqueous solutions of astringent therein, have received considerable attention in recent years because they exhibit the desired dry feel. However, improvements continue to be sought.

The present invention has as a primary objective improvements in the efficacy of antiperspirant compositions which comprise suspensions of astringent in a hydrophobic medium and emulsions of aqueous solutions of astringent in a hydrophobic medium as the continuous phase. It is another objective of the invention to improve the efficacy of such compositions wherein the continuous phase, or hydrophobic medium, comprises a liquid volatile silicone composition.

In accordance with these objectives, it has been discovered that antiperspirant compositions of the types represented by suspensions of astringent in a hydrophobic medium and emulsions of aqueous solutions of astringent in a hydrophobic medium have improved efficacy if there is incorporated therein a minor concentration of a $C_3$ to $C_8$ alkanediol compound.

Surprisingly, the advantages obtained by the incorporation of a $C_3$ to $C_8$ alkanediol into the composition of the invention are limited to a relatively narrow range of concentration, that is, from about 1% by weight to no more than about 5% by weight. In water-in-oil emulsion type compositions, the addition of appreciably more than about 5% of an alkanediol provides no benefit and may cause the emulsion to have an odor and, in both water-in-oil emulsion sticks and in suspension type sticks, may result in undesirable softness of the waxy matrix. If significantly less than about 1% by weight is used, the compositions do not exhibt enhanced efficacy. Preferably, the compositions will contain from about 2% to 3% by weight of the alkanediol.

Although the present invention will be described in detail with reference to antiperspirant stick compositions, it will be recognized that the invention in general relates to improving the efficacy of suspensions of astringent in a hydrophobic medium and emulsions of aqueous solutions of astringent in a hydrophobic medium and that such compositions may be formulated by well-known techniques into a variety of antiperspirant systems commonly available, such as creams, lotions, roll-ons, pump sprays, aerosols, and the like.

The alkanediols useful in the present invention are saturated $C_3$ to $C_8$ diols in which the hydroxyl groups are separated by no more than one carbon atom and which are compatible with the hydrophobic medium. Examples of suitable diols include 1,2-propanediol, 1,3-propanediol, 1,2-butanediol, 1,3-butanediol, 2,4-pentanediol, 2-methyl-2,4-pentanediol, 2,3-hexanediol, 1,3-hexanediol, 4,5-octanediol, and the like. The higher homologues are preferred, particularly hexylene glycol. Hexylene glycol (2-methyl-2,4-pentanediol) has been disclosed in U.S. Pat. No. 4,125,600 as an emollient in a dry powder aerosol composition containing aluminum chlorohydrate. However, its concentration is 32% of the non-propellant components. In the present invention, the use of hexylene glycol at such a high concentration is deleterious, particularly in water-in-oil emulsions, since it will cause the stick to become too soft, to have an odor, and, moreover, offers no beneficial result in terms of increased efficacy.

The term "hydrophobic medium," as used herein, means any of the commonly used water-insoluble oils, waxes, fatty alcohols, fatty acid esters, fatty acid amides, metal salts of fatty acids, volatile silicones, and the like, commonly used in the cosmetic art to prepare suspension and emulsion, so long as they are compatible with each other and with the emulsifying agents.

In the present invention, a preferred hydrophobic medium is a waxy matrix comprising a volatile cyclic polydimethylsiloxane oligomeric liquid, often referred to in the art as a volatile silicone. These are cyclic oligomers of dimethylsiloxane, examples of which are the cyclic tetramer (2,4,6,8-octamethylcyclotetrasiloxane, I), the cyclic pentamer (2,4,6,8,10-decamethylcyclopentasiloxane, II), and the cyclic hexamer (2,4,6,8,10,12- dodecamethylcyclohexasiloxane, III), and mixtures thereof, available from Dow Corning.

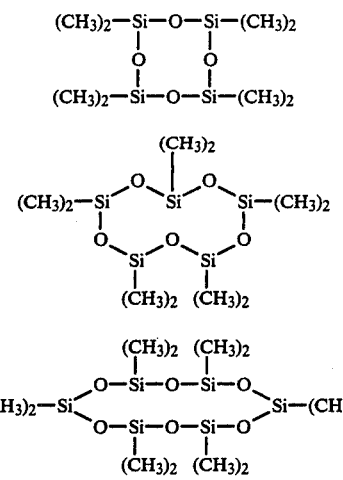

Certain linear silicone oils are also useful as the hydrophobic medium, alone or mixed with other compatible oils or cyclic silicones. Especially useful are certain volatile linear silicones having a boiling point at atmospheric pressure below 250° C., preferably between about 100° C. and 200° C.

The cyclic silicones are isolated from the hydrolysis product of dimethyldichlorosilane; see Patnode, Wilcock, *J. Am. Chem. Soc.* 68, 358 (1946).

Among the useful astringents are aluminum sulfate, aluminum chloride, aluminum chlorohydrate, aluminum sulfocarbolate, aluminum-zirconium chlorohydrate, zinc chloride, zinc sulfocarbolate, zinc sulfate, zirconium salts, such as zirconium chlorohydrate, combinations of aluminum chloride and aluminum-zirconium chlorohydrate, aluminum-zirconium chlorohydroglycine, and the like. Aluminum chlorohydrate is preferred. It may be used as an aqueous solution (generally 50%) or in granular or impalpable form. The aqueous solution is preferred.

The astringent material may be suspended in the hydrophobic medium or it may be emulsified therein as an aqueous solution. Where the astringent is suspended in the hydrophobic medium, the suspension may be improved, and a more homogeneous dispersion provided, if a suspending agent, such as a bentonite clay, for example, Bentone 27, 34, or 38, is incorporated also. In emulsion type compositions, of course, the astringent is predissolved in water and then emulsified in the hydrophobic medium.

The active ingredient may be used in amounts up to about 30% by weight on a solids basis, although normally from about 15% to 25% by weight on a solids basis, is used. In any case, sufficient should be used to provide at least a 20% reduction in perspiration in 50% of the population.

In addition to the volatile silicone, the hydrophobic medium used in an antiperspirant stick will contain a low melting waxy material compatible with the volatile silicone. While many waxy materials have been used in the preparation of antiperspirant sticks, the preferred waxy materials are long chain aliphatic alcohols, such as stearyl alcohol or cetyl alcohol.

EXAMPLE 1

Suspension Type Antiperspirant Stick

|  | Percent by Weight |
|---|---|
| 2-Methyl-2,4-pentanediol | 1.0 |
| Stearyl alcohol (95%) | 20.0 |
| Aluminum chlorohydrate | 25.0 |
| Aluminum chloride hexahydrate (50% aqueous solution) | 4.0 |
| Fumed silica | 0.2 |
| Cyclic silicone pentamer | 49.2 |
| Fragrance | 0.6 |
|  | 100.0 |

EXAMPLE 2

Suspension Type Antiperspirant Stick

|  | Percent by Weight |
|---|---|
| 2-Methyl-2,4-pentanediol | 1.0 |
| Stearyl alcohol (95%) | 20.0 |
| Aluminum chlorohydrate | 25.0 |
| Bentone 38 | 0.5 |
| Montan wax | 1.0 |
| Cyclic silicone pentamer | 51.9 |
| Fragrance | 0.6 |
|  | 100.0 |

EXAMPLE 3

Suspension Type Antiperspirant Stick

|  | Percent by Weight |
|---|---|
| 2-Methyl-2,4-pentanediol | 1.0 |
| Cetyl alcohol | 17.0 |
| Aluminum chlorohydrate | 15.0 |
| Aluminum chlorohydrate (50% aqueous solution) | 20.0 |
| Fumed silica | 1.0 |
| Cyclic silicone tetramer | 45.4 |
| Fragrance | 0.6 |
|  | 100.0 |

EXAMPLE 4

Water-in-Oil Emulsion Type Antiperspirant Stick

|  | Percent by Weight |
|---|---|
| Aluminum chlorohydrate (50% aqueous solution) | 50.0 |
| Polyglyceryl-4-isostearate | 2.0 |
| 2-Methyl-2,4-pentanediol | 2.0 |
| Stearic acid | 2.0 |
| Stearyl alcohol | 17.0 |
| Cyclic silicone pentamer | 26.0 |
| Mineral oil | 1.0 |
|  | 100.0 |

EXAMPLE 5

Water-in-Oil Emulsion Antiperspirant Stick

|  | Percent by Weight |
|---|---|
| Aluminum chlorohydrate (50% aqueous solution) | 50.0 |
| Polyglyceryl-4-isostearate | 2.0 |
| Stearic acid | 2.0 |

-continued

| | Percent by Weight |
|---|---|
| Stearyl alcohol | 17.0 |
| Cyclic silicone pentamer | 28.0 |
| Mineral oil | 1.0 |
| | 100.0 |

When the antiperspirant stick composition of Example 4 (containing 2-methyl-2,4-pentanediol) is compared with the antiperspirant stick composition of Example 5, it is found that the efficacy of the former is significantly higher than the latter.

EXAMPLE 6

Water-in-Oil Emulsion Antiperspirant Stick

| | Percent by Weight |
|---|---|
| Aluminum Chlorohydrate (50% aqueous solution) | 50.0 |
| Cyclic silicone pentamer | 26.0 |
| Stearyl alcohol | 19.0 |
| Polyglyceryl-4-oleate | 2.0 |
| 2-Methyl-2,4-pentanediol | 2.0 |
| Mineral oil | 1.0 |
| | 100.0 |

EXAMPLE 7

| | Percent by Weight |
|---|---|
| Aluminum chlorohydrate (50% aqueous solution) | 50.0 |
| Cyclic silicone pentamer | 26.1 |
| Stearyl alcohol | 18.5 |
| Polyglyceryl-4-oleate | 2.3 |
| Mineral oil | 2.0 |
| Stearic acid | 0.5 |
| Talc | 0.5 |
| Steareth-100* | 0.1 |
| | 100.0 |

*Stearyl alcohol condensed with an average of 100 moles of ethylene oxide

When the antiperspirant stick composition of Example 6 (containing 2-methyl-2,4-pentanediol) is compared with the antiperspirant stick composition of Example 7, it is found that the efficacy of the former is significantly higher than the latter.

What is claimed is:

1. An improved method for increasing the antiperspirant efficacy of a water-in-oil emulsion antiperspirant or suspension stick, selected from the group consisting of suspensions of an astringent compound in a hydrophobic medium and emulsions of an aqueous solution of an astringent compound in a hydrophobic medium, wherein the improvement comprises incorporating into said composition from about 1 to 5 percent by weight, based on the total weight of said composition, of a saturated $C_3$ to $C_8$ alkanediol compound; said diol compound having no more than one carbon atom separating the hydroxy groups thereof.

2. An improved method in accordance with claim 1 wherein said hydrophobic medium comprises a cyclic polydimethylsiloxane oligomer.

3. An improved method in accordance with claim 1 wherein said antiperspirant astringent is aluminum chlorohydrate, aluminum zirconium chlorhydrex or aluminum sesquichlorohydrate.

4. An improved method in accordance with claims 1, 2, or 3 wherein said hydrophobic medium additionally comprises a low-melting, water-insoluble wax compatible with said polydimethylsiloxane.

5. An improved method in accordance with claims 1, 2, 3, or 4 wherein said alkanediol is 2-methyl-2,4-pentanediol.

6. An improved water-in-oil antiperspirant emulsion stick composition comprising a hydrophobic medium, a metallic astringent compound, and wherein the improvement comprises from about 1 to 5 percent by weight, based on the total weight of said composition, of a saturated $C_3$ to $C_8$ alkanediol compound; said diol compound having no more than one carbon atom separating the hydroxy groups thereof.

7. A composition in accordance with claim 6 wherein said hydrophobic medium comprises a volatile cyclic polydimethylsiloxane oligomer.

8. A composition in accordance with claim 6 wherein said antiperspirant astringent is aluminum chlorohydrate, aluminum zirconium chlorhydrex or aluminum sesquichlorohydrate.

9. A composition in accordance with claim 6 wherein said hydrophobic medium additionally comprises a low-melting, water-insoluble wax compatible with said polydimethylsiloxane.

10. A composition in accordance with claim 6 wherein said alkanediol is 2-methyl-2,4-pentanediol.

* * * * *